United States Patent [19]

Myers

[11] 4,338,298

[45] Jul. 6, 1982

[54] VACCINE FOR PASSIVE IMMUNIZATION AGAINST ENTERIC COLIBACILLOSIS AND METHOD OF USE

[75] Inventor: Lyle L. Myers, Bozeman, Mont.

[73] Assignee: Endowment and Research Foundation at Montana State University, Bozeman, Mont.

[21] Appl. No.: 137,311

[22] Filed: Apr. 4, 1980

[51] Int. Cl.$^3$ .................. A61K 39/108; A61K 39/116

[52] U.S. Cl. .......................................... 424/92; 424/88

[58] Field of Search ........................ 424/92, 89, 87, 88

[56] References Cited

U.S. PATENT DOCUMENTS

| | | | |
|---|---|---|---|
| 3,293,129 | 12/1966 | Baker | 424/89 |
| 3,838,004 | 9/1974 | Mebus et al. | 424/89 |
| 3,839,556 | 10/1974 | Mebus et al. | 424/89 |
| 3,869,547 | 3/1975 | Mebus et al. | 424/89 |
| 3,873,422 | 3/1975 | Mebus | 424/89 |
| 3,914,408 | 10/1975 | Mebus | 424/89 |
| 3,919,412 | 11/1975 | Mebus | 424/89 |
| 3,919,413 | 11/1975 | Mebus | 424/89 |
| 4,298,597 | 11/1981 | Acres et al. | 424/92 |

OTHER PUBLICATIONS

Acres et al., Injection and Immunity, vol. 25, pp. 121–125, 1979.

Myers, L., Proceedings 2nd International Symposium on Neonatal Diarrhea, Oct. 3–5, 1978, U. of Saskatchewa, pp. 427–437.

Nagy, B., Injection and Immunity, vol. 27, pp. 21–24, 1980.

Myers et al., Am. J. Vet. Res., vol. 34, pp. 29–33, 1973.

Myers, L., Am. J. Vet. Res., vol. 39, pp. 761–765, 1978.

Myers, L., Am. J. Vet. Res., vol. 37, pp. 831–834, 1976.

*Primary Examiner*—Blondel Hazel

*Attorney, Agent, or Firm*—Lowe, King, Price & Becker

[57] ABSTRACT

A novel vaccine containing several *E. coli* K antigens for passively preventing enteric colibacillosis in a newborn food animal. Also disclosed is a method for using this vaccine that involves vaccinating the pregnant dam with the vaccine prior to the dam giving birth to the newborn animal. Passive immunization is produced in the newborn animal by antibodies stimulated by vaccination that pass in the colostrum to the newborn animal. The antibodies are specific for K antigens 30, 35, 85, and 99 present on the surface of the vaccinal strains of *E. coli.*

22 Claims, No Drawings

VACCINE FOR PASSIVE IMMUNIZATION AGAINST ENTERIC COLIBACILLOSIS AND METHOD OF USE

TECHNICAL FIELD

This invention relates to the prevention of enteric colibacillosis in newborn food animals such as calves and lambs.

BACKGROUND ART

Diarrheal disease in newborn food animals causes animal death and economic loss. In young beef and dairy calves, diarrheal disease is the leading cause of calf deaths in many areas of the world. While the etiology of the disease is not clearly defined, there are several different infectious agents capable of causing the clinical signs of diarrheal disease. Enterotoxigenic strains of *E. coli* have been found to be an important cause of acute diarrheal disease in calves under one week of age. This diarrhea in newborn animals such as calves may also be virus-caused, and it is known to prepare virus vaccines for prevention of the diarrhea. Exemplary of this type of work is U.S. Pat. No. 3,293,129, U.S. Pat. No. 3,838,004, U.S. Pat. No. 3,839,556, U.S. Pat. No. 3,869,547, U.S. Pat. No. 3,873,422, U.S. Pat. No. 3,919,412, U.S. Pat. No. 3,919,413 and U.S. Pat. No. 3,914,408.

Additionally, it is known to prevent enteric colibacillosis by a passive immunization technique wherein a pregnant dam is injected with a vaccine containing whole cells of killed enterotoxigenic *E. coli* (ETEC). In this regard, vaccines containing one strain or six strains of ETEC are known, with the following publications being illustrative. S. D. Acres et al, *Infection and Immunity,* 25:121–126 (July 1979); L. L. Myers, *Proceedings, 2nd International Symposium on Neonatal Diarrhea,* Oct. 3–5, 1978, University of Saskatchewan, pages 427–437; B. Nagy, *Infection and Immunity,* 27:21–24 (January 1980); L. L. Myers, *Am. J. Vet. Res.,* 34:29–33 (1973); L. L. Myers, *Am. J. Vet. Res.,* 39:761–765 (1978); and L. L. Myers, *Am. J. Vet. Res.,* 37:831–834 (1976). The first two of these publications show six strain vaccines containing at least 5 *E. coli* K antigens. These K antigens are K25, K85, K35, K28 and K30. These five K antigens are provided by equal amounts of five ETEC strains. As indicated in the below comparative example, which is taken from the second of these two publications, which is my own work, the K99 antigen is also present in my six strain vaccine for a total of at least six K antigens in that vaccine. The K99 antigen is also present in the six strain vaccine discussed in the Acres publication since this vaccine was formulated from the same serogroups used by me in my six strain vaccine. Thus, the six strain vaccine discussed by Acres also contains at least six K antigens.

However, this work and the other work of which I am aware is deficient in that it does not provide a vaccine containing several *E. coli* K antigens that is useful in the prevention of enteric colibacillosis, does not provide a vaccine of this type that causes an increased production of certain colostral antibodies in the dam of the newborn animal being protected, and does not provide a method for passive immunization against enteric colibacillosis using a vaccine containing several *E. coli* K antigens.

DISCLOSURE OF THE INVENTION

It is accordingly one object of the present invention to provide a vaccine containing several *E. coli* K antigens that is useful for preventing enteric colibacillosis.

Another object of the invention is to provide a vaccine of this type that causes an increased production of certain colostral antibodies in the dam of the newborn animal being protected.

A further object of the present invention is to provide a method for passive immunization against enteric colibacillosis using a vaccine containing several *E. coli* K antigens.

Other objects and advantages of the present invention will become apparent as the description thereof proceeds.

In satisfaction of the foregoing objects and objectives, there is provided by this invention a vaccine for the passive immunization of a newborn food animal against *E. coli*-caused diarrheal disease. This newborn animal is one that is susceptible to diarrheal disease caused by ETEC that contain K antigen 30, 35, 85 or 99. This vaccine includes four *E. coli* K antigens, these antigens being K30, K35, K85, and K99. The concentration of all of the antigens per milliliter of the vaccine, and the concentration of each of the antigens per milliliter of the vaccine are sufficient to effect the passive immunization by the stimulation of colostral antibodies reactive with *E. coli* K antigens 30, 35, 85 and 99, when the dam of the animal is injected prior to giving birth, with a quantity of the vaccine that produces the passive immunity. The vaccine also includes a physiologically acceptable aqueous carrier. Also provided by this invention is a method for the passive immunization of the newborn food animal against diarrheal disease caused by ETEC that contain K antigen 30, 35, 85 or 99. This method includes injecting the dam of the animal prior to the dam giving birth to the animal, with an amount of this vaccine sufficient to produce passive immunization of the newborn animal through colostral antibodies. The injection is timed so as to cause the increased production of colostral antibody titers in the dam sufficient to produce passive immunization of the animal, the antibodies being reactive with *E. coli* K antigens 30, 35, 85 and 99.

BEST MODE FOR CARRYING OUT THE INVENTION

The vaccine of the present invention is useful for the passive immunization of a newborn food animal against diarrheal disease caused by ETEC that contain K antigen 30, 35, 85 or 99. Exemplary animals are the calf and lamb.

This vaccine contains four *E. coli* K antigens. These antigens are K30, K35, K85 and K99. The K30, K35 and K85 antigens are polysaccharide capsular K antigens. These antigens are present on the surface of the *E. coli.* The K99 antigen is a proteinaceous pilus type of antigen present on the surface of the *E. coli.* All K antigen numbers used in designating these antigens are used in the international *E. coli* serotyping system for antigen designation.

The K antigens are suitably provided by whole cells of four different *E. coli* strains. These strains are a K99 antigen-containing strain, a K35 antigen-containing strain, a K30 antigen-containing strain, and a K85 antigen-containing strain. It is within the scope of this invention to provide these four *E. coli* K antigens using a microbiological carrier other than *E. coli.* In such a case, the carrier is genetically engineered using recombinant DNA techniques so as to bear the K antigens. The carrier could be engineered so that only one carrier is required, the one carrier bearing all four K antigens. Alternatively, each K antigen could be on its own microbiological carrier, as when whole cells of four different *E. coli* strains are used. Other possibilities exist such as two antigens on one carrier, with two carriers being required.

Alternatively, the K antigens are provided by whole cells of three different *E. coli* strains. These strains are a K35 antigen-containing strain, a K30 antigen-containing strain and a K85 antigen-containing strain, and at least one of these three strains also contains the K99 antigen. Thus, the present invention provides in either of these embodiments, a 3-strain or a 4-strain vaccine.

A particularly suitable K99 antigen-containing strain has the serogroup 0101:K-:K99. Illustratively, this serogroup is found in *E. coli* strain B41. A culture of *E. coli* B41 has been placed on permanent unrestricted deposit with the culture collection of the American Type Culture Collection (ATCC), 12301 Parklawn Drive, Rockville, Md. and has been assigned Accession No. ATCC-31619. This strain is hereinafter called *E. coli* strain B41.

An especially advantageous K35 antigen-containing strain has the serogroup 09:K35:K99. This serogroup is found, for example, in an *E. coli* strain that has been designated *E. coli* 21 in the culture collection of Montana State University. A culture of *E. coli* 21 has been placed on permanent unrestricted deposit with the culture collection of the American Type Culture Collection and has been assigned Accession No. ATCC-31616. This strain is hereinafter called *E. coli* strain 21.

A particularly useful K30 antigen-containing strain has the serogroup 0101:K30:K99. An exemplary strain of *E. coli* having this serogroup is designated *E. coli* 22 in the culture collection of Montana State University. A culture of *E. coli* 22 has been placed on permanent unrestricted deposit with the culture collection of the American Type Culture Collection and has been assigned Accession No. ATCC-31617. This strain is hereinafter called *E. coli* strain 22.

An especially suitable K85 antigen-containing strain has the serogroup 08:K85:K99. An illustrative *E. coli* strain with this serogroup is designated *E. coli* 23 in the culture collection of Montana State University. A culture of *E. coli* 23 has been placed on permanent unrestricted deposit with the culture collection of the American Type Culture Collection and has been assigned Accession No. ATCC-31618. This strain is hereinafter called *E. coli* strain 23.

As can be seen from the above description, any one of *E. coli* strains having the serogroup 09:K35:K99, 0101:K30:K99, and 08:K85:K99 could serve as the K99 antigen-containing strain. Thus a 3-strain vaccine is provided using only a 09:K35:K99 serogroup-containing strain, a 0101:K30:K99 serogroup-containing strain, and a 08:K85:K99 serogroup-containing strain. *E. coli* strains 21, 22 and 23 very advantageously provide a vaccine containing these strains.

An especially useful 4-strain vaccine contains a 0101:K-:K99 serogroup-containing strain, a 09:K35:K99 serogroup-containing strain, a 0101:K30:K99 serogroup-containing strain and a 08:K85:K99 serogroup-containing strain. A vaccine containing these strains is very suitably provided using *E. coli* strains B41, 21, 22 and 23.

In the vaccine of the present invention, *E. coli* K antigens 30, 35, 85 and 99 are present in a total concentration and are individually present in a concentration per milliliter of the vaccine sufficient to effect the passive immunization of the newborn food animal by the stimulation of colostral antibodies reactive with *E. coli* K antigens 30, 35, 85 and 99 when the dam of the newborn animal is injected prior to giving birth with a passive immunity-producing quantity of the vaccine. When the K antigens are provided by whole cells of several *E. coli* strains, about 25 mg, on a dry weight basis, of the whole cells per milliliter of the vaccine is a particularly advantageous total concentration. A concentration significantly above the 25 mg level may result in adverse reactions that include abortion. A particularly advantageous concentration of each of the four antigens per milliliter of the vaccine is a substantially equal amount.

The vaccine of the present invention also contains a physiologically acceptable aqueous carrier. It is very suitable to form the carrier from isotonic saline solution containing about 0.2 to 0.4% formalin.

A physiologically acceptable, whole cell binding adjuvant is used with particular advantage in the vaccine of the present invention that contains whole cells of *E. coli.* Illustratively, the adjuvant is aluminum hydroxide or $AlK(SO_4).12H_2O$, with aluminum hydroxide being especially advantageous. When aluminum hydroxide is used as the adjuvant, the vaccine contains about 1% of aluminum hydroxide. One way of adding the adjuvant to the vaccine is to combine about one part by volume of an about 3% aqueous solution of aluminum hydroxide with about two parts by volume of a suspension of the whole cells in the carrier.

As described above, the vaccine of the present invention contains both polysaccharide capsular K antigens and a proteinaceous antigen. This vaccine is advantageous over a proteinaceous antigen-containing vaccine such as is described in the publication of Acres discussed earlier since proteinaceous antigens may be easily lost during storage or under growth conditions. This is related to the fact that a proteinaceous antigen is plasmid controlled, whereas a polysaccharide antigen is chromosomally controlled.

The vaccine is prepared when the K antigens are provided by whole cells of *E. coli* strains, by growing each *E. coli* strain separately under aerobic conditions. This is carried out in a suitable growth medium for about twenty to twenty-four hours at about 37° C., with vigorous shaking of the growth medium. An exemplary growth medium is tryptic soy broth at pH 7.4. The cells are then advantageously killed by the addition of an agent that is suitably 0.2 to 0.4% formalin. Alternatively, the cells are attenuated, rather than killed, using conventional techniques. It is also within the scope of the present invention for the cells to be viable, the carrier being isotonic saline solution.

The cells are then harvested using centrifugation and suspended in the carrier described above. The amount of the carrier is determined by the desired concentration of the whole cells per milliliter of the vaccine. The cells are Gram-stained and reacted with specific antisera to verify that the proper K antigens are present. The concentrated cell suspensions are pooled in the proportions described above, and there is optionally added to the pooled cell suspension the adjuvant described above, in the amount described above.

Also provided by the present invention is a method for the passive immunization of the newborn food animal against diarrheal disease caused by ETEC that contain K antigen 30, 35, 85 or 99. This method involves injecting the dam of the animal prior to the dam giving birth with an amount of the vaccine of the present invention that is sufficient to passively immunize the animal against the diarrheal disease. For purposes of this specification, the term "injection" means a subcutaneous and/or intramuscular injection. About 5 milliliters of the vaccine is especially useful for the injection when the vaccine contains about 25 mg, on a dry weight basis, of whole cells per milliliter.

The injection is timed so as to cause increased production of colostral antibodies in the dam sufficient to passively immunize the newborn animal. The colostral antibodies stimulated are reactive with *E. coli* K antigens 30, 35, 85, and 99. Although more than two injections can be used and the time between injections varied greatly, it is sufficient to use two injections for a dam that has not been previously injected with the vaccine, and it is preferred that the two injections be administered at a minimum of about 2 to 3 weeks apart, with the second injection being given about 2 to 4 weeks prior to the expected date of giving birth. If the dam has previously been injected with the vaccine, say, as a result of a course of vaccination during a prior gestation, then one injection is sufficient. This injection is preferably given about 2 to 4 weeks before the expected date of giving birth. Additional injections may be used in either situation but no appreciable benefit results.

The below Examples are illustrative of the vaccine and method of the present invention. Unless otherwise stated, all percentages in these Examples and throughout this specification, are volume/volume. Furthermore, unless otherwise indicated, all processing steps are conducted at ambient temperature and pressure. It is to be understood that these Examples are merely illustrative and are not in any way to be interpreted as limiting the scope of the invention.

EXAMPLE 1

*E. coli* strains B41, 21, 22 and 23 are grown separately in tryptic soy broth (Difco Laboratories, Detroit, Mich.) under aerobic conditions at 37° C. for twenty hours, with vigorous shaking of the broth growing mediums. The cells are killed by the addition of 0.3% formalin, harvested using centrifugation and resuspended in isotonic saline solution containing 0.3% formalin to give 40 mg of cells, on a dry weight basis, per ml of cell suspension. The cells are Gram-stained and reacted with a specific antiserum to be sure that the proper K antigen is present. An equal volume of each of the four concentrated cell suspensions is pooled, and there is added to two parts by volume of the pooled cell concentrates, 1 part by volume of a 3% aqueous solution of aluminum hydroxide. The vaccine contains approximately 25 mg of cells, on a dry weight basis, per ml.

EXAMPLE 2

Twenty-one pregnant Hereford beef cows are given two 5 ml injections of the vaccine of Example 1 five weeks and two weeks before the first calf is born. The injections are given using a ½ to ⅝ inch, 16 gauge needle and are partly subcutaneous and partly intramuscular. At six to twelve hours of age, each colostrum-fed, newborn animal is orally challenge inoculated with approximately $5\times10^{10}$ viable cells of either enterotoxigenic *E. coli* (ETEC) strain 21 (serogroup 09:K35:K99), or ETEC strain designated 251 in the culture collection of Montana State University and having a serogroup of 08:K85:K99. The strain used for the challenge inoculation is grown aerobically in tryptic soy broth (Difco Laboratories, Detroit, Mich.) at 37° C. for twelve to thirty-six hours prior to challenge inoculation. The calves are observed for clinical signs of disease for three days following inoculation. A rating of 0 is given to a calf that does not develop clinical signs of enteric disease. A rating of 1 is given to a calf that develops a transient diarrhea (usually for a duration of twelve to twenty-four hours) but that develops no other clinical signs of disease. A rating of 2 is given to a diarrheic calf that becomes dehydrated (sunken eyes) and depressed. A rating of 3 is given to a severely dehydrated calf that is too weak to stand. An animal given a rating of 2 or 3 is considered to have acute enteric colibacillosis. As shown in Table 1, there were not any calves that developed acute enteric disease whose dams were given the vaccine.

For comparison, twenty cows are given two 5 ml injections of a placebo prepared by mixing 2 parts by volume of isotonic saline solution containing 0.3% formalin with one part by volume of a 3% aqueous solution of aluminum hydroxide. The other procedures set forth in the previous paragraph are followed. As shown in Table 1, 70% of the calves developed acute enteric colibacillosis.

Also for comparison purposes a 1-strain vaccine prepared from only *E. coli* strain B41 is injected into 21 cows. This vaccine is prepared in exactly the same manner as the 4-strain vaccine of Example 1, except, of course, there is not any pooling of the cells of different strains, with this vaccine also containing approximately 25 mg of cells, on a dry weight basis, per ml. The procedures set forth in the first paragraph of this Example are followed, and as shown in Table 1, 33% of the calves whose dams were given this vaccine developed acute enteric disease. The geometric mean K99 agglutinating antibody titer, in the colostrum is 28.7. This value is approximately one half of the magnitude of the K99 titer induced by the 4-strain vaccine (55.7). The geometric means of the K99 titer for the 7 cows whose calves developed acute enteric disease is 10.3, whereas the K99 titer for the other 14 cows is 48.0.

COMPARATIVE EXAMPLE

A 6-strain vaccine containing 25 mg (dry weight) of cells per ml is prepared using ETEC isolates of the following serogroups: 09:K35:K99, 0101:K30:K99, 08:K85:K99, 020:K?:K99, 08:K25:K99 and 0101:K28:K99. Each isolate is grown aerobically in tryptic soy broth (Difco Laboratories, Detroit, Mich.) at 37° C. for twenty-four hours. The cells are killed by the addition of 0.3% formalin, centrifuged and resuspended in isotonic saline-formalin (0.3%) solution.

TABLE 1

| Treatment of cows | No. of cow-calf pairs | ETEC challenge strain | No. of calves given each disease rating | | | |
|---|---|---|---|---|---|---|
| | | | 0 | 1 | 2 | 3 |
| 4-strain vaccine | 21 | 21 | 7 | 4 | 0 | 0 |
| | | 251 | 7 | 3 | 0 | 0 |
| 1-strain vaccine | 21 | 21 | 2 | 6 | 0 | 3 |
| | | 251 | 3 | 3 | 1 | 3 |
| Placebo | 20 | 21 | 0 | 4 | 0 | 6 |
| | | 251 | 0 | 2 | 1 | 7 |

TABLE 2

| Treatment of cows | No. of cow-calf pairs | Volume of challenge (ml) | No. of calves given each disease rating | | | |
|---|---|---|---|---|---|---|
| | | | 0 | 1 | 2 | 3 |
| 6-strain vaccine | 2 | 2 | 0 | 2 | 0 | 0 |
| | 1 | 3 | 1 | 0 | 0 | 0 |
| | 3 | 4 | 1 | 1 | 1 | 0 |
| | 4 | 6 | 2 | 1 | 1 | 0 |
| | | | 4 | 4 | 2 | 0 |
| Placebo (same as used in Example 2) | 2 | 2 | 0 | 2 | 0 | 0 |
| | 1 | 3 | 0 | 0 | 1 | 0 |
| | 3 | 4 | 0 | 1 | 1 | 1 |
| | 3 | 6 | 0 | 1 | 0 | 2 |
| | | | 0 | 4 | 2 | 3 |

An equal weight of each of the six isolates is used in preparing the vaccine. An adequate amount of 3% aluminum hydroxide is added to bind all of the pooled cells. The resulting vaccine has 25 mg, on a dry weight basis, of the whole cells per ml.

Ten pregnant Hereford cows are injected intramuscularly with 5 ml of the 6-strain vaccine at five weeks and two weeks prior to the herd calving date. Colostrum-fed newborn calves are orally challenge inoculated at three to five hours of age with 1 to $3\times10^{10}$ viable cells of *E. coli* strain 21. The strain used for the challenge inoculation is grown aerobically in tryptic soy broth (Difco Laboratories, Detroit, Mich.) at 37° C. for twelve to twenty-four hours prior to challenge inoculation. Calves are observed for clinical signs of disease for 4 to 5 days following challenge. As shown in Table 2 (which essentially uses the rating system discussed above), 20% of the calves whose dams were given this vaccine developed acute enteric disease. Other details concerning the results of this comparative experimentation are contained in L. L. Myers, *Proceedings, 2nd International Symposium on Neonatal Diarrhea,* Oct. 3–5, 1978, University of Saskatchewan, pages 427–437. The pertinent portion of this publication that presents these additional details, particularly the details concerning colostral antibody titers, is hereby incorporated by reference into this application.

EXAMPLE 3

The efficacy of the vaccine of Example 1 against naturally occurring diarrheal disease in beef herds is shown as follows. A group of pregnant cows in eleven privately owned beef herds is given two 5 ml subcutaneous injections of the vaccine at approximately three weeks and one week prior to the expected herd calving date. Each herd experienced significant losses due to enteric disease during 1978, and ETEC was isolated from calves in a majority of these herds during 1978. As shown in Table 3, of the 676 newborn calves of these cows, 5 died of diarrheal disease and a total of 17 developed acute enteric disease.

For comparison purposes, another group of pregnant cows in these eleven herds is injected with the placebo used in Example 2, using two 5 ml subcutaneous injections at approximately three weeks and one week prior to the expected herd calving date. As shown in Table 3, of the 699 newborn calves of these cows, 16 died of diarrheal disease and a total of 34 developed acute enteric disease.

Also for comparison, another group of pregnant cows in ten of these eleven herds and in another herd is injected with the 1-strain vaccine used in Example 2, using two 5 ml subcutaneous injections at approximately three weeks and one week prior to the expected calving date. Of the 664 newborn calves of these cows, 9 died of diarrheal disease and a total of 32 developed acute enteric disease. The geometric means K99 agglutinating antibody titer is 32.0. This is more than one half of the magnitude of the K99 titer induced by the 4-strain vaccine (54.5).

Thus, we have unexpectedly discovered in carrying out this experimentation and that set forth in Example 2 above that the four *E. coli* K antigen-containing vaccine of the present invention produces a higher K99 colostral antibody titer than does a 1-strain vaccine prepared from only *E. coli* strain B41.

Applicability

This invention is useful for the prevention of *E. coli*-caused diarrheal disease.

TABLE 3

| Herd No. | No. of calves | Severity of diarrheal disease in calves | | | | Deaths due to diarrheal disease |
|---|---|---|---|---|---|---|
| | | 0 | 1 | 2 | 3 | |
| 4-strain vaccine | | | | | | |
| 1 | 13* | 11 | 2 | 0 | 0 | 0 |
| 2 | 22*+ | 22 | 0 | 0 | 0 | 0 |
| 3 | 25* | 19 | 3 | 3 | 0 | 0 |
| 4 | 55*≠ | 55 | 0 | 0 | 0 | 0 |
| 5 | 50 | 48 | 0 | 2 | 0 | 0 |
| 6 | 27 | 25 | 2 | 0 | 0 | 0 |
| 7 | 105* | 105 | 0 | 0 | 0 | 0 |
| 8 | 30 | 28 | 0 | 0 | 2 | 2 |
| 9 | 50* | 50 | 0 | 0 | 0 | 0 |
| 10 | 24φ | 3 | 14 | 6 | 1 | 0 |
| 11 | 275* | 191 | 81 | 0 | 3 | 3 |
| Total | 676 | 557 | 102 | 11 | 6 | 5 |
| Placebo | | | | | | |
| 1 | 21 | 12 | 6 | 2 | 1 | 0 |
| 2 | 23 | 15 | 1 | 6 | 1 | 1 |
| 3 | 27 | 21 | 4 | 2 | 0 | 0 |
| 4 | 55 | 55 | 0 | 0 | 0 | 0 |
| 5 | 50 | 49 | 0 | 1 | 0 | 0 |
| 6 | 30 | 28 | 2 | 0 | 0 | 0 |
| 7 | 108 | 108 | 0 | 0 | 0 | 0 |
| 8 | 29 | 25 | 0 | 0 | 4 | 4 |
| 9 | 50 | 50 | 0 | 0 | 0 | 0 |
| 10 | 21 | 6 | 3 | 7 | 5 | 6 |
| 11 | 275 | 195 | 75 | 0 | 5 | 5 |
| Total | 699 | 574 | 91 | 18 | 16 | 16 |

*Herds in which ETEC was isolated during 1978.

+ Significantly fewer ($P<0.005$) calves in this group developed enteric disease than in the control group.

≠ Cows in this herd received only the first vaccination; vaccine and placebo intended for the second vaccination were apparently lost in shipment to the ranch.

φ Significantly fewer ($P<0.005$) deaths due to enteric disease occurred in this group as compared with the controls in this herd.

I claim:

1. A vaccine for the passive immunization of a newborn food animal against *E. coli*-caused diarrheal disease, said animal being susceptible to diarrheal disease caused by enterotoxigenic *E. coli* that contain K antigen 30, 35, 85 or 99, said vaccine consisting essentially of:

(a) four *E. coli* K antigens, these antigens being K30, K35, K85 and K99; the concentration of all of said antigens per ml of said vaccine and of each of said antigens per ml of said vaccine being sufficient to effect said passive immunization by the stimulation of colostral antibodies reactive with *E. coli* K antigens 30, 35, 85, and 99, when the dam of said animal is injected prior to giving birth to said animal with a quantity of said vaccine that produces said passive immunization; and (b) a physiologically acceptable aqueous carrier.

2. The vaccine of claim 1 wherein said K antigens are provided by whole cells of four different *E. coli* strains, said strains being a K99 antigen-containing strain, a K35 antigen-containing strain, a K30 antigen-containing strain and a K85 antigen-containing strain.

3. The vaccine of claim 2 wherein said K99 antigen-containing strain has the serogroup 0101:K-:K99.

4. The vaccine of claim 2 wherein said K35 antigen-containing strain has the serogroup 09:K35:K99.

5. The vaccine of claim 2 wherein said K30 antigen-containing strain has the serogroup 0101:K30:K99.

6. The vaccine of claim 2 wherein said K85 antigen-containing strain has the serogroup 08:K85:K99.

7. The vaccine of claim 2, wherein said *E. coli* strains are a 0101:K-:K99 serogroup-containing strain, a 09:K35:K99 serogroup-containing strain, a 0101:K30:K99 serogroup-containing strain and a 08:K85:K99 serogroup-containing strain.

8. The vaccine of claim 7 wherein said strains of *E. coli* are ATCC-31616, ATCC-31617, ATCC-31618, and ATCC-31619.

9. The vaccine of claim 2 further comprising a physiologically acceptable, whole-cell binding adjuvant, said adjuvant being present in an amount sufficient to bind the total amount of said whole cells.

10. The vaccine of claim 9 wherein said adjuvant is aluminum hydroxide.

11. The vaccine of claim 1 wherein said carrier is formed from isotonic saline solution containing about 0.2 to 0.4% formalin.

12. The vaccine of claim 2 wherein the whole cells of each of said *E. coli* strains are present in a substantially equal amount.

13. The vaccine of claim 2 wherein said concentration of said whole cells per ml of said vaccine is about 25 mg, on a dry weight basis, per ml.

14. The vaccine of claim 1 wherein said animal is a calf or a lamb.

15. The vaccine of claim 1 wherein said animal is a calf.

16. A method for the passive immunization of a newborn food animal against *E. coli*-caused diarrheal disease, said newborn animal being susceptible to diarrheal disease caused by enterotoxigenic *E. coli* that contain K antigen 30, 35, 85 or 99, said method comprising the injection of the dam of said animal prior to said dam giving birth to said animal, with an amount of the vaccine of claim 1 sufficient to produce said passive immunization through colostral antibodies; the injection being timed so as to cause the increased production of colostral antibodies in the dam sufficient to produce said passive immunization; said antibodies being reactive with *E. coli* K antigens 30, 35, 85 and 99.

17. The method of claim 16 wherein the dam is injected twice at a minimum of about 2 to 3 weeks apart.

18. The method of claim 16 wherein the dam is injected once.

19. The method of claim 17 wherein the second injection is about 2 to 4 weeks prior to the expected birth date.

20. The method of claim 16 wherein there is injected about 5 ml of said vaccine, which contains about 25 mg, on a dry weight basis, of said whole cells per ml.

21. The vaccine of claim 16 wherein said animal is a calf or a lamb.

22. The vaccine of claim 16 wherein said animal is a calf.

* * * * *